United States Patent
Salman

(10) Patent No.: US 6,929,800 B2
(45) Date of Patent: Aug. 16, 2005

(54) NASAL PASSAGE CLEANING COMPOSITION

(76) Inventor: Abdul Rasoul Salman, 500 Brownsville Rd., Apalachicola, FL (US) 32320

( * ) Notice: Subject to any disclaimer, the term of this patent is extended or adjusted under 35 U.S.C. 154(b) by 144 days.

(21) Appl. No.: 09/923,227

(22) Filed: Aug. 6, 2001

(65) Prior Publication Data

US 2003/0031730 A1 Feb. 13, 2003

(51) Int. Cl.$^7$ .......................... A61F 13/00; A01N 59/16; A01N 59/08; A01N 59/06
(52) U.S. Cl. ...................... 424/434; 424/400; 424/422; 424/641; 424/642; 424/680; 424/698; 424/725; 424/747; 514/849; 514/946; 514/947
(58) Field of Search ................................ 424/641, 642, 424/643, 747, 400, 449, 78.02

(56) References Cited

U.S. PATENT DOCUMENTS

| | | | |
|---|---|---|---|
| 4,029,095 A | | 6/1977 | Pena |
| 4,403,611 A | | 9/1983 | Babbitt et al. |
| 4,432,968 A | | 2/1984 | Page et al. |
| 4,956,385 A | | 9/1990 | Eby, III |
| 5,310,419 A | | 5/1994 | McCoy et al. |
| 5,322,689 A | * | 6/1994 | Hughes et al. .............. 424/401 |
| 5,322,697 A | | 6/1994 | Meyer |
| 5,622,724 A | * | 4/1997 | Bryce-Smith ............... 424/641 |
| 5,693,318 A | | 12/1997 | Burke et al. |
| 5,705,170 A | | 1/1998 | Kong et al. |
| 5,720,963 A | | 2/1998 | Smith |
| 5,840,278 A | | 11/1998 | Coleman |
| 5,891,427 A | | 4/1999 | Mettler |
| 5,895,408 A | | 4/1999 | Pagan |
| 5,897,858 A | | 4/1999 | Haslwanter et al. |
| 5,912,007 A | * | 6/1999 | Pan et al. .................... 424/440 |
| 5,948,414 A | | 9/1999 | Wiersma |
| 6,013,632 A | * | 1/2000 | Jones et al. .................. 514/17 |
| 6,071,541 A | | 6/2000 | Murad |
| 6,103,218 A | | 8/2000 | Brucker et al. |
| 6,125,843 A | | 10/2000 | Gold et al. |
| 6,156,293 A | | 12/2000 | Jutila et al. |
| 6,156,792 A | | 12/2000 | Hatton et al. |
| 6,183,766 B1 | | 2/2001 | Sine et al. |
| 6,187,332 B1 | | 2/2001 | Gern et al. |
| 6,344,210 B2 | * | 2/2002 | Fust ........................... 424/435 |

* cited by examiner

*Primary Examiner*—Michael Hartley
*Assistant Examiner*—Sharmila S. Gollamudi
(74) *Attorney, Agent, or Firm*—William J. Sapone; Coleman Sudol Sapone PC

(57) ABSTRACT

A nasal passage cleaning composition according to the invention comprises water and salt as a base, and contains a mucolytic agent such as alum and/or zinc sulphate to shrink the mucosa and allow sinus passage drainage, decreasing pressure in the infected sinus an alleviates sinus headache and face ache. A preferred mucolytic agent is n-acetyl-L-cystine, which is used to dissolve or soften mucus in the nasal passages, though methyl salicylate may also be used to disintegrate crusted mucus, acting also as a topical anti-inflammatory agent and as a pain relieving agent to reduce pain and discomfort.

2 Claims, No Drawings

NASAL PASSAGE CLEANING COMPOSITION

TECHNICAL FIELD

This invention relates to a composition for cleaning the nasal passages.

BACKGROUND

Rhinosinusitis is the most common health care complaint in the United States affecting approximately one out of eight persons at some time in their lives. Many people also suffer from nasal and sinus allergies and their complications such as bronchitis, colds, ear aches, sinusitis and sinus headaches. Various medicaments have been proposed to treat the nasal passages. For example, nasal steroid sprays are available for treating allergies, but these have undesirable side-effects such as loss of smell, loss of activity of cilia, increased incidence of viral infection, nose bleeds, etc. In addition, it may take several days or weeks before a benefit is obtained using steroids.

An alpha stimulant or vasoconstrictor such as ephedrine, NeoSynephrine® (phenylephrine hydrochloride) or Afrin (oxymetazoline hydrochloride) may be used as a decongestant, but these have various possible side-effects such as increased blood pressure, heart irregularities and rebound phenomenon and use beyond three days is not generally advised.

Sea water was traditionally used to rinse the nasal passage as part of a treatment for sinus problems but seawater alone lacks effectiveness. Significant discomfort is associated with seawater rinsing.

What is needed is a composition that can be used to clean and clear the nose and sinus passages with a minimum of discomfort, and without the side effects common with existing nasal treatments.

SUMMARY OF THE INVENTION

It is an object of the present invention to provide a nasal passage cleaning composition, which does not utilize steroids.

It is another object to provide a nasal passage cleaning composition containing natural ingredients in a comfortable pH isotonic solution to avoid significant discomfort.

It is a further object to provide a method for cleaning the nasal passages using a composition which avoids significant side effects.

These and other objects of the present invention are achieved by a nasal passage cleaning composition comprising a water and salt base, a mucolytic, an antiseptic, a non-steroidal, anti-inflammatory, and optionally, a decongestion, an antipruritic and an analgesic, the composition formulated to have a comfortable, generally near neutral, pH. Other ingredients may be used in addition to those listed above such as an aroma agent and a pain reliever. Utilizing the present invention, nasal passage cleaning can be undertaken by spraying, rinsing or douching, with minimized discomfort, additionally avoiding the significant side-effects associated with steroidal nasal sprays, or vasoconstrictors like ephedrine or NeoSynephrine sprays or drops.

DETAILED DESCRIPTION OF THE INVENTION

The invention is a nasal passage cleaning composition for individual use. Generally, the nasal organ functions as a filter, capturing and preventing particulates and other material from entering the lungs. The nose also acts as a detector by utilizing the sense of smell. When clogged or overburdened with particulates or when subject to disease, mucus can build up with a consequent reduction in filtering ability, loss of the sense of smell and blockage of nasal airways which forces mouth breathing and prevents the flow of sinus secretions which is critical in reducing bacterial and fungal infection.

A nasal passage cleaning composition according to the invention comprises water and salt as a base, and contains a mucolytic agent such as alum and/or zinc sulphate to shrink the mucosa and allow sinus passage drainage, decreasing pressure in the infected sinus and alleviates sinus headache and face ache. A preferred mycolytic agent is n-acetyl-L-cysteine, which is used to dissolve or soften mucus in the nasal passages, though methyl salicylate may also be used to disintegrate crusted mucus, acting also as a topical anti-inflammatory agent and as a pain relieving agent to reduce pain and discomfort.

An antiseptic, such as tea tree oil, menthol, peppermint oil, camphor, alcohol, zinc sulfate and/or glycerine are also used. Some of these compounds provide multiple functions. For example, camphor acts to relieve pain and discomfort and also acts as an astringent. Tea tree oil also provides an aromatizing ingredient while glycerine is useful as an emollient/moisturizer which protects the mucosa of the nose and sinuses. Menthol is used as an aromatizer and as an astringent and antipruritic. Balsam tolu is a useful emollient/mucosal protectant that is also an aromatizer. Potassium alum, zinc sulfate or zinc chloride can be used as an astringent and decongestant.

Preferably, the composition is buffered with a citric or phosphate compound to achieve a comfortable pH of the composition, which is generally at or near a neutral pH, i.e. having a pH in the range of about 6.0 to 6.4.

Various optional or substitute ingredients could include gum benzoin, menthol, peppermint oil , thymol, various antipruritics, etc. Tea tree oil is a preferred ingredient, though substitutes are available which could include eucalyptol, cinnamon, aloe, pine or spearmint oil.

An more preferred composition would include zinc sulfate between 0.1 and 3 grams per liter, glycerine at 5 to 50 grams per liter, gum benzoin, camphor or menthol between 0.01 and 0.1 grams per liter, aloe between 0.4 and 4 grams per liter, a solvent such as alcohol between 0.5 and 3 milliliters per liter, and tea tree oil and methyl salicylate between 0.1 and 2 milliliters per liter.

Utilizing the present invention, cleaning of the nasal passages is accomplished with less discomfort than associated with other nasal cleaning products and without using steroids with their associated side effects. By spraying, rinsing or douching the nasal passages with the inventive composition, the result is dissolution and removal of pollen, smog, dust and other pollutants which cause allergies and decongestion of the nose, opening the sinus orifices for better drainage and a decrease in sinus pressure to relieve sinus headaches.

A preferred composition according to the invention is illustrated in Table 1, though the invention is not limited to these particular ingredients or amounts, as discussed previously:

TABLE 1

| | | |
|---|---|---|
| 1000 | ml | Water |
| 7.1 | grams | Sodium Chloride |
| 0.5 | ml | Methyl Salicylate |
| 0.8 | ml | Tea Tree Oil |
| 0.023 | grams | Gum Benzoin or Balsam Tolu |
| 0.025 | grams | Camphor |
| 0.03 | grams | Menthol or Peppermint Oil |
| 20 | ml | Glycerine |
| 1.6 | grams | Potassium Alum |
| 1 | gram | Zinc Sulphate |
| 0.1 | grams | n-acetyl-L-cystine |
| 1 | gram | Alcohol* |

*Alcohol could be substituted by adding a solvent for camphor and menthol or removed by using a surfactant such as polysorbate 80, also known as Tween 80, chlorobutanol or sodium lauryl sulphate.

Once formulated, the composition may be applied using an applicator commonly used for nasal passage irrigation, or using a spray bottle or other like apparatus. As the composition enters the nasal passages, mucus and other residue in the nasal passages is softened and removed, the nasal passages once rinsed, are decongested and generally the user is able to breath more freely, and has a refreshing feeling. Depending on the user's condition, application a few times per day, once per day, once per week or once every two weeks can assure optimum relief for the user.

While preferred embodiments of the present invention have been shown and described, it will be understood by those skilled in the art that various modifications can be made without varying from the scope of the invention.

What is claimed is:

1. A non-steroidal nasal passage cleaning composition comprising per 1000 ml. of water, 7.1 grams sodium chloride, 0.5 ml. methyl cylate 0.8 ml tea tree oil, 0.023 grams gum benzoin or balsam tolu, 0.025 grams camphor, or, 0.03 grams camphor, 0.03 grams menthol or peppermint oil, 20 ml. glycerin, 1.6 grams potassium alum, 1 gram zinc sulfate, 0.1 grams n-acetyl 1. cystine and 1 gram of alcohol.

2. A method for cleaning the nasal passages comprising providing a non-steroidal nasal passage cleaning composition comprising, per 1000 ml. of water, 7.1 grams sodium chloride, 0.5 ml. methyl salicylate, 0.8 ml tea free oil, 0.023 grams gum benzoin or balsam tolu, 0.025 grams camphor, 0.03 grams menthol or peppermint oil, 20 ml. glycerin, 1.6 grams potassium alum, 1 gram zinc sulfate, 0.1 grams n-acetyl 1. cystine and 1 gram of alcohol; and, spraying the nasal passage with the cleaning composition.

* * * * *